United States Patent
Greenberg et al.

(10) Patent No.: US 7,904,163 B2
(45) Date of Patent: Mar. 8, 2011

(54) RETINAL PROSTHESIS WITH SEPARATE CENTRAL ELECTRODE ARRAY AND PERIPHERAL ELECTRODE ARRAY

(75) Inventors: Robert Jay Greenberg, Los Angeles, CA (US); Mark S. Humayun, Glendale, CA (US)

(73) Assignee: Second Sight Medical Products, Inc, Sylmar, CA (US)

( * ) Notice: Subject to any disclaimer, the term of this patent is extended or adjusted under 35 U.S.C. 154(b) by 1155 days.

(21) Appl. No.: 11/418,677

(22) Filed: May 4, 2006

(65) Prior Publication Data

US 2006/0253172 A1     Nov. 9, 2006

Related U.S. Application Data

(60) Provisional application No. 60/677,551, filed on May 4, 2005.

(51) Int. Cl.
*A61N 1/05*     (2006.01)

(52) U.S. Cl. .......................................................... 607/54

(58) Field of Classification Search ................. 607/1–3, 607/50, 53–54, 65, 115–116, 139–141, 148; 600/373, 375, 377, 382–383, 386, 390, 393
See application file for complete search history.

(56) References Cited

U.S. PATENT DOCUMENTS

| | | | |
|---|---|---|---|
| 4,573,481 A | 3/1986 | Bullara | |
| 4,628,933 A | 12/1986 | Michelson | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,718,209 B2 * | 4/2004 | Williamson et al. | 607/54 |
| 7,003,355 B1 * | 2/2006 | Suaning et al. | 607/54 |
| 7,149,586 B2 * | 12/2006 | Greenberg et al. | 607/116 |
| 7,228,181 B2 * | 6/2007 | Greenberg et al. | 607/54 |
| 7,338,522 B2 * | 3/2008 | Greenberg et al. | 623/6.63 |
| 2002/0111658 A1 | 8/2002 | Greenberg et al. | |
| 2002/0198573 A1 * | 12/2002 | Nisch et al. | 607/54 |
| 2003/0158588 A1 * | 8/2003 | Rizzo et al. | 607/54 |
| 2003/0187491 A1 | 10/2003 | Greenberg et al. | |
| 2003/0233134 A1 * | 12/2003 | Greenberg et al. | 607/36 |
| 2004/0106965 A1 * | 6/2004 | Chow | 607/54 |

FOREIGN PATENT DOCUMENTS

WO     WO 03/061537 A1     7/2003

OTHER PUBLICATIONS

Park, et al., A Foveated-structure CMOS Retina Chip for Edge Detection with Local Light Adaptation,Elsevier, Senors and Actuators A 108 (2003) 75 80, 3 pages (double-sided).

* cited by examiner

*Primary Examiner* — Carl H Layno
*Assistant Examiner* — Jessica Sarcione
(74) *Attorney, Agent, or Firm* — Scott B. Dunbar

(57) ABSTRACT

The artificial percept of light may be created by electrically stimulating the neurons of the retina. While a photolithographed array internal to the retina provides superior resolution, an array external to the retina provides easier implantation and improved manufacturability. Therefore it is advantageous to supply a high-resolution electrode array internal to the sclera, near the fovea and a lower-resolution electrode array eternal to the sclera near the periphery of the retina.

24 Claims, 3 Drawing Sheets

RETINAL PROSTHESIS WITH SEPARATE CENTRAL ELECTRODE ARRAY AND PERIPHERAL ELECTRODE ARRAY

CROSS REFERENCE TO RELATED APPLICATION

This application claims the benefit U.S. Provisional Patent Application No. 60/677,551, filed May 4, 2005 entitled Retinal Prosthesis with Internal Central Electrodes and External Peripheral Electrodes, which is hereby incorporated herein by reference. This application is related to U.S. patent application Ser. No. 09/783,236 filed Feb. 13, 2001, now U.S. Pat. No. 7,338,522, entitled Implantable Retinal Electrode Array Configuration for Minimal Retinal Damage and Method of Reducing Retinal Stress and U.S. patent application Ser. No. 10/112,801, filed Mar. 28, 2002, now U.S. Pat. No. 7,148,586, entitled Variable Pitch Electrode Array, and U.S. patent application Ser. No. 11/413,689, filed Apr. 28, 2006, entitled Flexible Circuit Electrode, which are hereby incorporated herein by reference.

This application is related to U.S. patent application Ser. No. 09/783,236 filed Feb. 13, 2001, entitled Implantable Retinal Electrode Array Configuration for Minimal Retinal Damage and Method of Reducing Retinal Stress and U.S. patent application Ser. No. 10/112,801, filed Mar. 28, 2002, entitled Variable Pitch Electrode Array, and U.S. patent application Ser. No. 11/413,689, filed Apr. 28, 2006, entitled Flexible Circuit Electrode, which are hereby incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to a visual prosthesis and more specifically to an improved mechanical and electrical configuration for retinal prosthesis for artificial vision.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Normann describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Humayun, U.S. Pat. No. 5,935,155 describes the use of retinal tacks to attach a retinal array to the retina. Alternatively, an electrode array may be attached by magnets or glue. U.S. Pat. No. 5,109,844 to de Juan describes a flat electrode array placed against the retina for visual stimulation.

A human retina naturally provides very high-resolution near the fovea at the center of vision. Resolution near the periphery is much lower and is primarily designed to detect movement. When our peripheral vision detects movement, we move first our eyes, and then our heads toward the movement, detecting the object with our fovea. This happens so quickly and automatically, that we are generally unaware of the lower resolution in the periphery. Further, we tend to scan a scene and our brain remembers details after they are scanned by the fovea. This gives us the perception of continuous high-resolution vision.

Photolithographic techniques are the best know technique for creating an electrode array that approaches the natural resolution of the fovea. However, photolithographic techniques require that the array be made flat, not curved like the retina. Other techniques such a silicone molding over hand welded wires are easily made curved, but can not produce the high-resolution of a photolithographic array.

Further, it is necessary to implant electronic drivers for the electrodes external to the eye as the vitreous within the eye will not efficiently dissipate the heat of the electronics. It is difficult to pass a large number of wires through the sclera because the incision, or scleratomy, much heal and seal around those wires.

SUMMARY OF THE INVENTION

The artificial percept of light may be created by electrically stimulating the neurons of the retina. While a photolithographed array internal to the retina provides superior resolution, an array external to the retina provides easier implantation and improved manufacturability. Therefore it is advantageous to supply a high-resolution electrode array internal to the sclera, near the fovea and a lower-resolution electrode array eternal to the sclera near the periphery of the retina.

The preferred method of manufacturing a high-resolution electrode array is through photolithography, which requires the array to be made flat. While it is possible to curve the array afterward, it is difficult and costly. I small high-resolution array can be implanted near the fovea. Due to its small size, curvature is less of an issue. A larger lower-resolution array can be molded in silicone or similar method and placed around the periphery, of the retina, where the retina is naturally lower-resolution. Further, the lower-resolution array can be implanted external to the sclera reducing the number of electrical connectors passing through the sclera.

Even if a separate lower-resolution array is implanted internal to the sclera, super-choroidal (between the choroid and sclera) or intra-scleral (between the layers of the sclera), it is easier to make a lower-resolution array in a curved shape.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
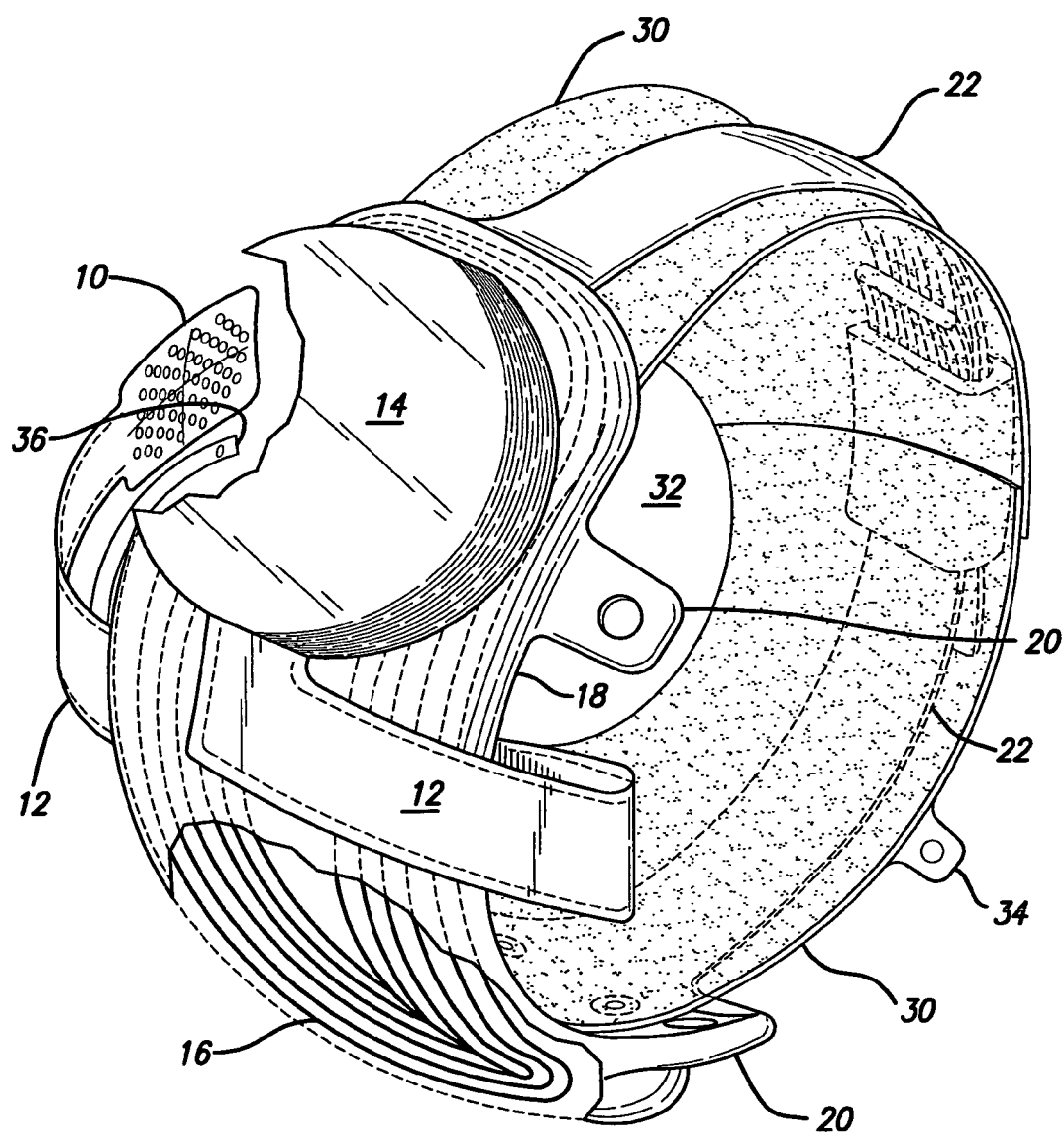
FIG. 1 is a perspective view of the implanted portion of the preferred retinal prosthesis.

FIG. 1 shows a perspective view of the implanted portion of the preferred retinal prosthesis. A high-resolution electrode array 10 is mounted by a retinal tack or similar means to the epiretinal surface near the fovea. The high-resolution electrode array 10 is electrically coupled by a cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil may be made from a thin film polymer sandwich with wire traces deposited between layers of thin film polymer. The electronics package 14 and secondary inductive coil 16 are held together by a molded body 18. The molded body 18 may also include suture tabs 20. The molded body narrows to form a strap 22, which surrounds the sclera and holds the molded body 18, secondary inductive coil 16, and electronics package 14 in place. The strap 22 further supports a lower-resolution electrode array 30, mounted external to the sclera. The lower-resolution electrode array 30 surrounds the peripheral retina and supports electrodes for stimulating percepts in the periphery of the retina. The external electrode array is preferable molded of silicone in a curved shape and highly flexible. The molded body 18, suture tabs 20 strap 22 and lower-resolution electrode array 30 are preferably an integrated unit made of silicone elastomer. Silicone elastomer can be formed in a pre-curved shape to match the curvature of a typical sclera. However, silicone remains flexible enough to accommodate implantation and to adapt to variations in the curvature and size of an individual sclera. The secondary inductive coil 16 and molded body 18 are preferably oval shaped. A strap can better support an oval shaped coil.

The lower-resolution array 30 may be integrally molded into the strap 22 or a separate structure, which passes under the strap 22. The lower-resolution electrode array 30 may extend both in front of the strap to the pars plana and behind the strap to cover all of the retina leaving a gap 32 over that portion of the retina stimulated by the high-resolution electrode array and the optic nerve. Ideally, the lower-resolution electrode array extends beyond the portion of the strap 22 that passes through the buckle 23, to provide full 360° stimulation. The lower-resolution electrode array 30 may overlap itself to accommodate different size scleras. After implantation, overlapping electrodes may be disabled. Particularly, if the lower-resolution electrode array 30 is separate from the strap 22, it would be advantageous to provide suture tabs 34 directly on the lower-resolution electrode array 30.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. It is an advantage of the present design, that the entire implanted portion of the prosthesis is attached to and supported by the sclera. The lower-resolution electrode array 30, though mounted externally, must move with the retina to give a consistent visual image. Also, by placing the device under the rectus muscles with the electronics package in an area of fatty issue between the rectus muscles, eye motion does not cause any flexing which might fatigue, and eventually damage, the device.

It is further advantageous to provide a remote return or common electrode for each electrode array on the opposite side of the retina from the electrode array, thereby causing current to flow through the retina. For the high-resolution array 10, the outer case of the electronics package 14 provides a remote return electrode. For the lower-resolution electrode array 30, remote return electrode 36 may be placed internal to the eye. Alternatively, the lower-resolution electrode array 30 may provide the remote return electrode for the high-resolution array 10, and the high-resolution array 10 may provide the remote return electrode for the lower-resolution array 30.

Figure 2:
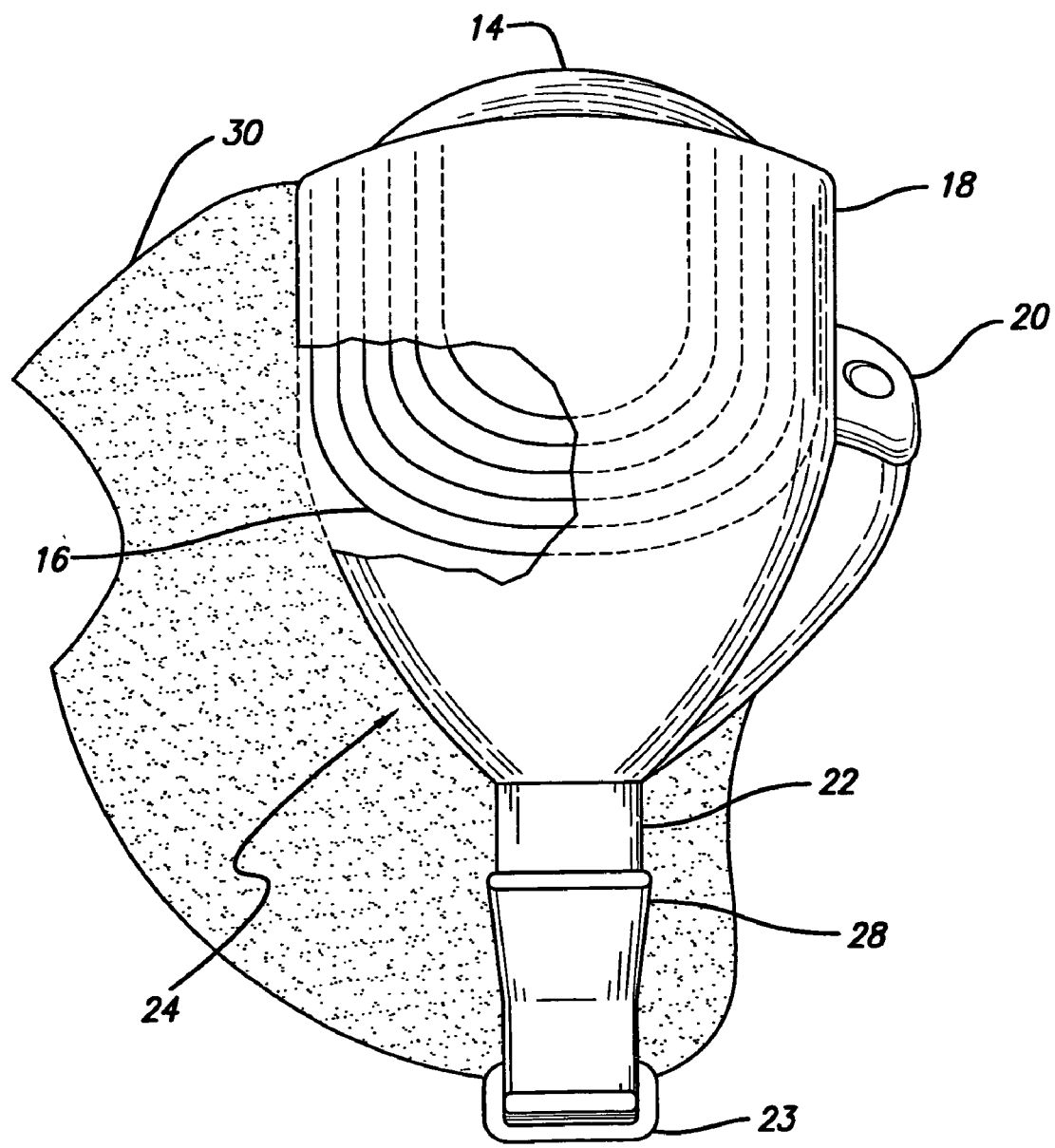
FIG. 2 is a side view of the implanted portion of the preferred retinal prosthesis showing the fan tail in more detail.

FIG. 2 shows a side view of the implanted portion of the retinal prosthesis, in particular, emphasizing the fan-tail 24 and the shape of the lower-resolution electrode array 30. When implanting the retinal prosthesis, it is necessary to pass the strap 22 and lower-resolution electrode array 30 under the eye muscles to surround the sclera. The secondary inductive coil 16 and molded body 18 must also follow the strap under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body is shaped in the form of a fan tail 24 on the end opposite the electronics package 14.

Reinforced attachment points 26 are provided to facilitate handling of the retinal prosthesis by surgical tools. Preferably, the reinforced attachment points are harder silicone formed around holes through the molded body 18. Further, a hook 28 is molded into the strap 22 just beyond the end of the fan tail 24. A surgical tool can be used against the hook 28 to push the strap 22 under the rectus muscles. The hook 28 is more clearly depicted by the edge view of FIG. 3. The strap 22 is attached to itself by a sleeve 23. The sleeve 23 is a friction device that connects two silicone bands and holds them together with friction. The sleeve 23 is similar to a Watzke sleeve, used with a scleral buckle, and is well known in the art.

In the preferred embodiment, the high-resolution electrode array 10 and cable 12 are formed layers of a thin polymer film with metal traces sandwiched between the thin polymer films. In such an embodiment, it is advantageous that the film with openings for high-resolution electrode array 10 be the same film with an opening for connection to the electronics package 14. Therefore, the cable 12 exits the electronics package up away from the fantail 24, folds over itself and exits down toward the fantail 24, before turning at a right angle and piercing the sclera. This allows the same side of the cable to face both the electronics package and the retina. The cable 12 may also include a fantail at the point it is attached to the electronics package 14 and at the point it is attached to the high-resolution electrode array 10 to reduce any stress on the connections that may be caused by implantation. It is important that the cable exit the molded body 18 toward the front of the eye. The cable must travel above the lateral rectus muscle and pierce the sclera at the pars plana, in front of the retina, so it does not damage the retina. Once inside the eye, the cable 12 can fold back over the retina to properly locate the high-resolution electrode array 10 on the epiretinal surface.

Fundamentally, the lower the resolution of the array, the easier it is to form the array to shape of the retina. While described here as two arrays, one higher resolution and less flexible, and one lower-resolution and more flexible, it possible to use more than two arrays using more than two array technologies. Its is also possible to use the same array technology and tile segments to achieve a rounder overall shape. With thin film technology curving the array, after deposition of the metal traces can cause the traces to break. Hence, the prosthesis may provide a high-resolution array, a middle resolution array and a lower-resolution array or even more variations.

It may be advantageous to use two thin film arrays, a small higher resolution array with very thin metal traces and a lower-resolution thin film array with more curvature and more robust metal traces.

The lower resolution electrode array may be a photolithographically-made thin film array. While it is difficult to curve a thin film in two dimensions to follow the spherical shape of the retina, it is easy to curve a thin film in one dimension, such as a cylinder. Hence, a thin film can be used to make a generally cylindrical array around the periphery of the retina, either externally or internally to the retina.

Figure 3:
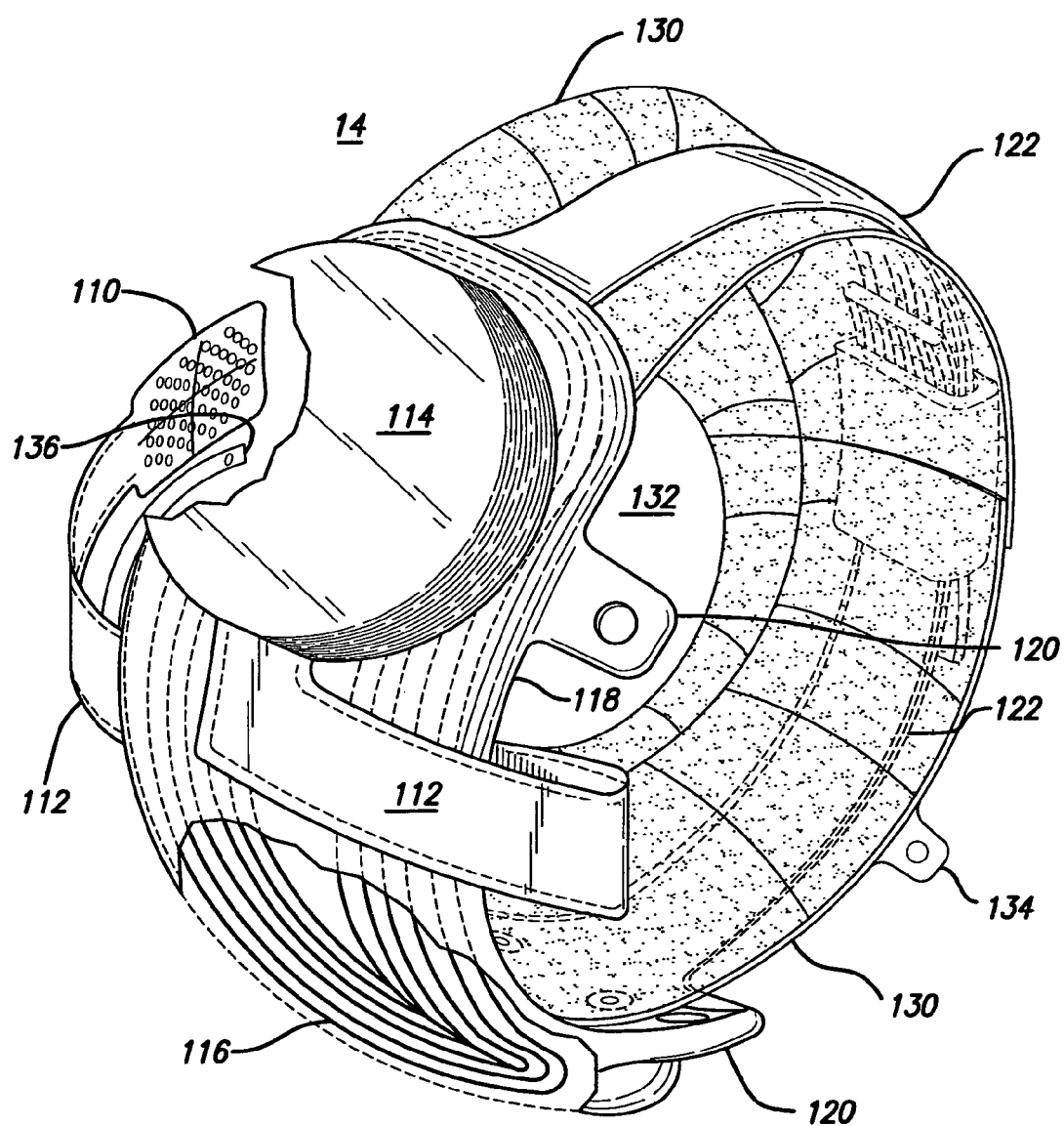
FIG. 3 is a perspective view of an alternate embodiment of the implanted portion of a retinal prosthesis.

Alternatively, as shown in FIG. 3, the lower-resolution array 130 may be tiled small sections of thin film arrays. A high-resolution electrode array 110 is mounted by a retinal tack or similar means to the epiretinal surface near the fovea. The high-resolution electrode array 110 is electrically coupled by a cable 112, which pierces the sclera and is electrically coupled to an electronics package 114, external to the sclera.

The electronics package 114 is electrically coupled to a secondary inductive coil 16. The electronics package 114 and secondary inductive coil 116 are held together by a molded body 18. The molded body 118 may also include suture tabs 120. The molded body narrows to form a strap 122, which surrounds the sclera and holds the molded body 118, secondary inductive coil 116, and electronics package 114 in place. The strap 122 further supports a lower-resolution electrode array 130, mounted external to the sclera. The lower-resolution electrode array 130 surrounds the peripheral retina and supports electrodes for stimulating percepts in the periphery of the retina. The lower-resolution electrode array is preferable tiled sections of thin film array, which are sufficiently small that they conform to the curvature of the retina. The lower-resolution electrode array 130 may extend both in front of the strap to the pars plana and behind the strap to cover the entire retina leaving a gap 132 over that portion of the retina stimulated by the high-resolution electrode array and the optic nerve. Ideally, the lower-resolution electrode array extends beyond the portion of the strap 122 that passes through the buckle 123, to provide full 360° stimulation. The lower-resolution electrode array 130 may overlap itself to accommodate different size scleras. After implantation, overlapping electrodes may be disabled. Particularly, if the lower-resolution electrode array 130 is separate from the strap 122, it would be advantageous to provide suture tabs 134 directly on the lower-resolution electrode array 130.

While the preferred embodiment provides for the lower-resolution array to be external to the sclera, it is advantageous to provide multiple arrays of different technologies even if they are all implanted on the epi-retinal surface. It is also possible to provide differing implantation methods for different array types. Options for implantation include epi-retinal, sub-retinal, super-choroidal, intra-scleral and extra-scleral. Epi-retinal is on the inner retinal surface in the vitreous humor. Sub-retinal is on the outer retinal surface between the retina and the choroid. Super-choroidal is between the choroid and sclera. Intra-scleral in within the layers of the sclera. Extra-scleral is outside the sclera. Each implantation location provides unique advantages and disadvantages. It should be clear to one of skill in the art that the array technologies and array placements may be combined in many permutations to achieve any desired result.

Accordingly, what has been shown is an improved retinal prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A retinal prosthesis comprising:
   a high-resolution electrode array including a plurality of electrodes suitable to be mounted internal to a sclera in close proximity to a fovea of a retina and to stimulate visual percepts on the retina;
   a lower-resolution electrode array including a plurality of electrodes suitable to be mounted in close proximity to a periphery of the retina and to stimulate visual percepts on the retina, when the high-resolution electrode array is mounted internal to the sclera in close proximity to the fovea of the retina; and
   implantable electronics for driving said high-resolution electrode array and said lower-resolution electrode array,
   wherein the high-resolution electrode array and the lower-resolution electrode array are physically distinct and separate electrode arrays.

2. The retinal prosthesis according to claim 1, wherein said high-resolution electrode array is suitable to be mounted in a epi-retinal location.

3. The retinal prosthesis according to claim 1, wherein said high-resolution electrode array is suitable to be mounted in a sub-retinal location.

4. The retinal prosthesis according to claim 1, wherein said lower-resolution electrode array is suitable to be mounted external to the sclera.

5. The retinal prosthesis according to claim 1, wherein said lower-resolution electrode array is suitable to be mounted in a super-choroidal location.

6. The retinal prosthesis according to claim 1, wherein said high-resolution electrode array is made from thin film polymer with metal traces patterned by photolithographic process.

7. The retinal prosthesis according to claim 1, wherein said lower-resolution electrode array is formed from wire molded in silicone.

8. The retinal prosthesis according to claim 1, wherein said lower-resolution electrode array is formed in a single unit with said implantable electronics.

9. The retinal prosthesis according to claim 1, further comprising suture tabs connected to the implantable electronics suitable for attaching the implantable electronics to the sclera.

10. The retinal prosthesis according to claim 1, wherein a cable supplying said high-resolution electrode array and said high-resolution electrode array comprise metal traces sandwiched between thin polymer films.

11. The retinal prosthesis according to claim 1, wherein said lower-resolution electrode array is more flexible than said high-resolution electrode array.

12. The retinal prosthesis according to claim 1, wherein said lower-resolution electrode array has a rounder shape than said high-resolution electrode array.

13. The retinal prosthesis according to claim 12, wherein both said higher-resolution electrode array and said lower-resolution electrode array are thin film arrays including metal traces, wherein the metal traces of said lower-resolution electrode array are more robust than the metal traces of said high-resolution electrode array.

14. The retinal prosthesis according to claim 12, wherein said high-resolution array is a thin film array and said lower-resolution electrode array includes tiled small sections of thin films arrays.

15. A retinal prosthesis comprising:
   a high-resolution electrode array including a plurality of electrodes suitable to be mounted internal to a sclera in close proximity to a fovea of a retina and to stimulate visual percepts on the retina;
   a lower-resolution electrode array including a plurality of electrodes suitable to be mounted in close proximity to a periphery of the retina and to stimulate visual percepts on the retina, when the high-resolution electrode array is mounted internal to the sclera in close proximity to the fovea of the retina;
   an electronics package suitable to be mounted external to the sclera;
   an electrical cable coupling said high-resolution electrode array to said electronics package; and
   a secondary inductive coil, electrically coupled to said electronics package and suitable to be mounted to a side of the sclera;
   wherein the high-resolution electrode array and the lower-resolution electrode array are physically distinct and separate electrode arrays.

16. The retinal prosthesis according to claim 15, further comprising a strap connected to said secondary inductive coil suitable for surrounding the sclera.

17. The retinal prosthesis according to claim 15, further comprising a strap connected to said lower-resolution electrode array suitable for surrounding the sclera.

18. The retinal prosthesis according to claim 15, further comprising a strap connected to said electronics package suitable for surrounding the sclera.

19. The retinal prosthesis according to claim 15, further comprising suture tabs connected to said secondary inductive coil suitable for attaching said secondary inductive coil to the sclera.

20. The retinal prosthesis according to claim 15, wherein said cable is folded to present a same side of said cable to both said electronics package and the retina.

21. The retinal prosthesis according to claim 15, wherein said electrical cable is suitable to pierce a pars plana region of the sclera.

22. The retinal prosthesis according to claim 15, wherein said high-resolution electrode array is suitable to be placed in an epiretinal location.

23. The retinal prosthesis according to claim 15, wherein said lower-resolution electrode array is suitable to be mounted external to the sclera.

24. A retinal prosthesis comprising:
- a high-resolution electrode array including a plurality of electrodes suitable to be mounted internal to a sclera in close proximity to a fovea of a retina and to stimulate the visual percepts on the retina;
- a plurality of tiled lower-resolution electrode arrays each including a plurality of electrodes suitable to be mounted in close proximity to a periphery of the retina and to stimulate visual percepts on the retina, when the high-resolution electrode array is mounted internal to the sclera in close proximity to the fovea of the retina;
- an electronics package suitable to be mounted external to the sclera; and
- an electrical cable coupling said high-resolution electrode array, and said plurality of lower-resolution electrode arrays to said electronics package;
- wherein the high-resolution electrode array and the plurality of tiled lower-resolution electrode arrays are each physically distinct and separate electrode arrays.

* * * * *